US011737823B2

(12) United States Patent
Wong

(10) Patent No.: US 11,737,823 B2
(45) Date of Patent: Aug. 29, 2023

(54) ANTENNA SYSTEMS AND METHODS OF USE

(71) Applicant: INTUITIVE SURGICAL OPERATIONS, INC., Sunnyvale, CA (US)

(72) Inventor: Serena H. Wong, Los Altos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 341 days.

(21) Appl. No.: 16/669,057

(22) Filed: Oct. 30, 2019

(65) Prior Publication Data

US 2020/0155232 A1 May 21, 2020

Related U.S. Application Data

(60) Provisional application No. 62/753,511, filed on Oct. 31, 2018.

(51) Int. Cl.

*A61B 18/18* (2006.01)
*A61B 18/00* (2006.01)
*A61B 34/20* (2016.01)
*A61B 34/35* (2016.01)

(52) U.S. Cl.

CPC .......... *A61B 18/1815* (2013.01); *A61B 34/20* (2016.02); *A61B 34/35* (2016.02); (Continued)

(58) Field of Classification Search

CPC ........... A61B 2018/00023; A61B 2018/00035; A61B 2018/1846; A61B 2018/00577; A61B 18/1815

See application file for complete search history.

(56) References Cited

U.S. PATENT DOCUMENTS 5,800,494 A * 9/1998 Campbell .......... A61B 18/1815 607/101
6,380,732 B1 4/2002 Gilboa
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Jaymi E Della
*Assistant Examiner* — Abigail M Ziegler
(74) *Attorney, Agent, or Firm* — Haynes and Boone, LLP

(57) ABSTRACT

An antenna system for tissue ablation includes an energy transmission member, a conductive hollow coil member, and a fluid cooling system. The energy transmission member has an inner conductor, an outer conductor, and a dielectric layer between the inner and outer conductors. A portion of the dielectric layer extends distally of a distal end of the outer conductor. The conductive hollow coil member includes a member lumen within a length of the conductive hollow coil member. The conductive hollow coil member is coiled around the portion of the dielectric layer and is separate from the inner conductor. The conductive hollow coil member extends along an entire length of the outer conductor of the energy transmission member. The fluid cooling system is coupled to the conductive hollow coil member for providing a flow of a cooling fluid through the member lumen for cooling the conductive hollow coil member.

20 Claims, 10 Drawing Sheets

FLUID COOLING SYSTEM 120 136 100A 114 104 108 124 134 102A 126 118A 128 110 122 129A 127 132A 130A 106

FLUID COOLING SYSTEM 120 136 100B 114 104 108 124 126 134 102B 110 118B 128 130B 122 127 131 129B 132B 106

(52) U.S. Cl.
CPC ............... *A61B 2018/00023* (2013.01); *A61B 2018/00029* (2013.01); *A61B 2018/00035* (2013.01); *A61B 2018/00351* (2013.01); *A61B 2018/00446* (2013.01); *A61B 2018/00494* (2013.01); *A61B 2018/00511* (2013.01); *A61B 2018/00523* (2013.01); *A61B 2018/00529* (2013.01); *A61B 2018/00541* (2013.01); *A61B 2018/00559* (2013.01); *A61B 2018/00577* (2013.01); *A61B 2018/183* (2013.01); *A61B 2018/1846* (2013.01); *A61B 2018/1861* (2013.01)

(56) References Cited

U.S. PATENT DOCUMENTS 6,389,187 B1 5/2002 Greenaway et al.
7,311,703 B2 * 12/2007 Turovskiy .......... A61B 18/1815 606/33
7,416,681 B2 8/2008 Kim et al.
7,772,541 B2 8/2010 Froggatt et al.
8,900,131 B2 12/2014 Chopra et al.
9,259,274 B2 2/2016 Prisco
9,452,276 B2 9/2016 Duindam et al.
2005/0055020 A1 * 3/2005 Skarda ............... A61B 18/1492 606/41
2006/0013523 A1 1/2006 Childlers et al.
2008/0266203 A1 * 10/2008 Rossetto ............ A61B 18/1815 343/895
2009/0082762 A1 * 3/2009 Ormsby ................. H01Q 11/08 606/33
2009/0222002 A1 * 9/2009 Bonn ................. A61B 18/1815 606/33
2011/0213352 A1 * 9/2011 Lee .................... A61B 18/1815 606/33
2012/0004651 A1 * 1/2012 Shiu ................... A61B 18/1815 606/33
2020/0205894 A1 * 7/2020 Eaton-Evans ...... A61B 18/1815
2021/0153936 A1 * 5/2021 Mosesov ............ A61B 18/1815

* cited by examiner

ANTENNA SYSTEMS AND METHODS OF USE

CROSS-REFERENCE TO RELATED APPLICATIONS

This application claims the benefit of U.S. Provisional Application 62/753,511 filed Oct. 31, 2018, which is incorporated by reference herein in its entirety.

FIELD

The present disclosure is directed to minimally invasive ablation systems and methods of use.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Minimally invasive medical tools may also include ablation instruments. Ablation instruments transmit energy in the form of electromagnetic waves to a targeted area of tissue, such as a tumor or other growth, within the patient anatomy to destroy the targeted tissue. Some minimally invasive medical tools and ablation instruments may be teleoperated or otherwise computer-assisted. Various features may improve the effectiveness of minimally invasive ablation instruments.

SUMMARY

Embodiments of the invention are best summarized by the claims that follow the description.

In some examples, an antenna system for tissue ablation may include an energy transmission member, a conductive hollow coil member coupled to the energy transmission member, and a fluid cooling system coupled to the conductive hollow coil member for providing a flow of cooling fluid through a member lumen of the conductive hollow coil member for cooling the conductive hollow coil member.

In some examples, an antenna system for tissue ablation may include an energy transmission member, an antenna body coupled to the energy transmission member, and a choke extending around the energy transmission member, the choke including a conductive tubular coil member including a member lumen extending through the conductive tubular coil member and adapted to convey a cooling fluid.

In some examples, a method of transferring energy to an ablation target site may include conducting energy through an energy transmission member, radiating energy from a conductive hollow coil member, wherein the conductive hollow coil member includes a member lumen extending through the conductive hollow coil member, and wherein the conductive hollow coil member is coupled to the energy transmission member, and providing a flow of cooling fluid from a fluid cooling system through the member lumen for cooling the conductive hollow member.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1A:
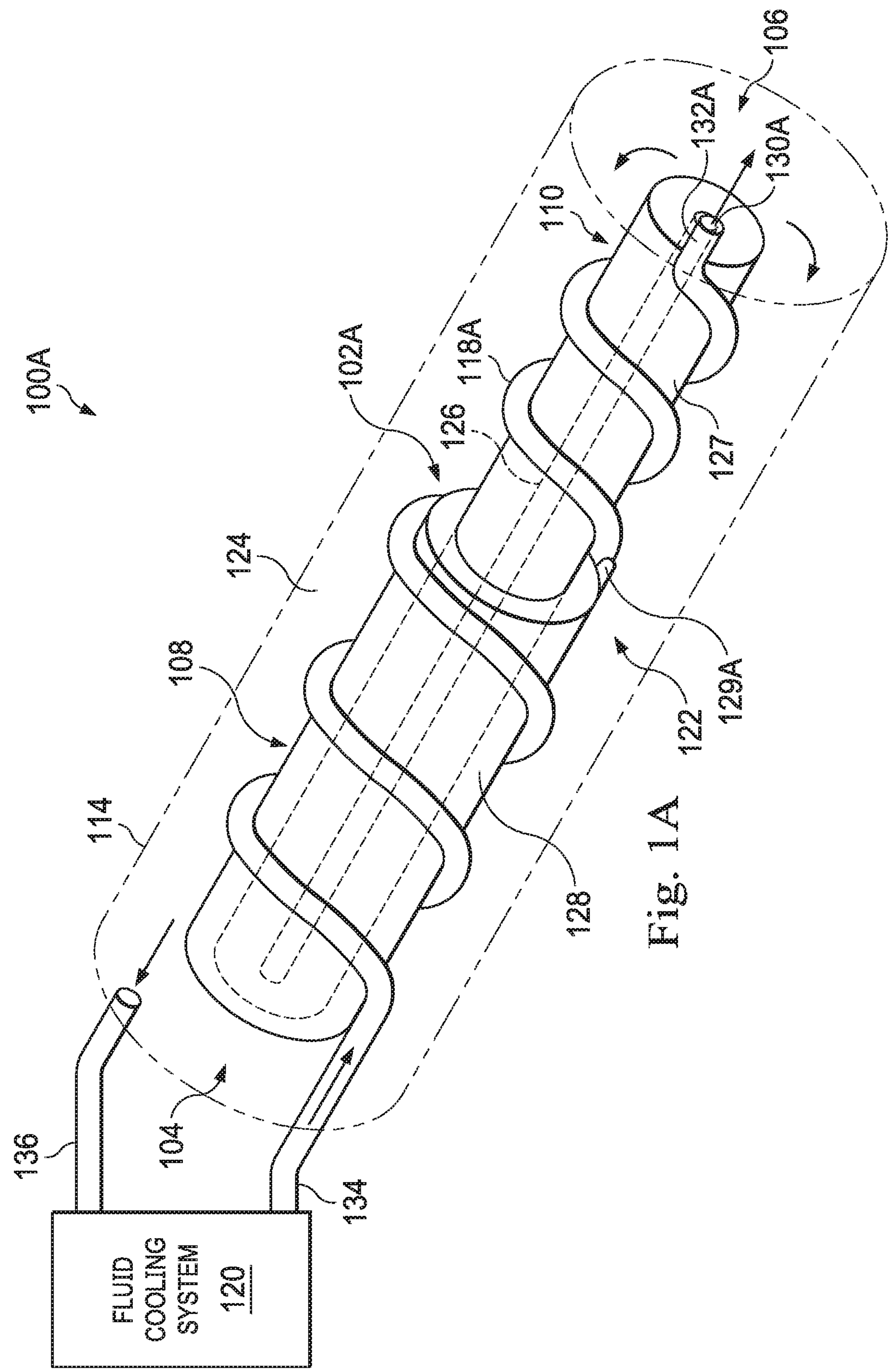
FIG. 1A illustrates an antenna system for tissue ablation with an antenna body coupled to an outer conductor according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIGS. 1A, 1B, 1C, 2A, 2B, 3, 4, 5, and 6 are perspective view of antenna systems according to some embodiments. In some embodiments, the antenna systems are used for tissue ablation, causing an increase in a temperature of an anatomic target area by transmitting electromagnetic waves from the antenna system to the anatomic target area, or ablation site. In some embodiments, antenna systems may be flexible and suitable for use in, for example, surgical, diagnostic, therapeutic, ablative, and/or biopsy procedures. In some embodiments, the antenna systems may be used as a medical instrument in an image-guided medical procedure performed with a teleoperated medical system as described in further detail below. While some embodiments are provided herein with respect to such procedures, any reference to medical or surgical instruments and medical or surgical methods is non-limiting. In some embodiments, the antenna systems may be used for non-teleoperational procedures involving traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIG. 1A, an antenna system 100A generally includes a flexible antenna instrument 102A which includes an antenna body 118A coupled to an elongate energy transmission member 122. The antenna instrument 102A extends between a proximal end 104 and a distal end 106. The elongate energy transmission member includes an outer conductor 128 substantially surrounding a dielectric layer 127 and an inner conductor 126 in a proximal portion 108 of the elongate energy transmission member 122. In this embodiment, the dielectric layer 127 and the inner conductor 126 extend distally beyond the outer conductor 128 forming a distal portion 110 of the elongate energy transmission member 122. In the distal portion 110, the inner conductor 126 and dielectric layer 127 are not surrounded by outer conductor 128. In this embodiment, elongate energy transmission member 122 is a coaxial cable but for simplicity, jacket layers and other details may be omitted. Other coaxial cable configurations with different configurations, shapes, etc. of inner conductor, outer conductor, and dielectric layers could also be used. In alternative embodiments, any type of elongate energy transmission member 122 may be used for antenna instrument 102.

In this embodiment, antenna body 118A is electrically coupled (e.g., soldered) to outer conductor 128 by an electrical coupling 129A. Antenna body 118A may be used to radiate microwave energy for use in the tissue ablation process. More specifically, antenna body 118A can be used to create electromagnetic radiation within a wavelength range of one meter to one millimeter, and within a frequency range of approximately 300 Megahertz (MHz) TO 300 Gigahertz (GHz) (e.g., a microwave). A microwave, which is a type of radio wave, is made up of a magnetic field at a right angle to an electric field, and both the magnetic field and the electric field oscillate at a specific frequency and travel together along a direction that is perpendicular to both the magnetic field and the electric field. In some embodiments, the wavelength and the frequency of the microwaves being radiated by antenna body 118A may be modified to cause a desired type of ablation at the ablation target site.

In this embodiment, antenna body 118A is a conductive coiled hollow antenna that includes a lumen 130A terminating at a distal outlet 132A. The lumen 130A may have a circular cross section or any other shape providing an open lumen. In the example shown in FIG. 1A, the antenna system 100A includes a fluid cooling system 120 in fluid communication with the antenna body 118A. More specifically, the lumen 130A provides a conduit for fluid from the fluid cooling system 120 to flow to the outlet 132A.

In this embodiment, antenna body 118A is coiled around the distal portion 110 of elongate energy transmission member 122. In this example, antenna body 118A is tightly coiled around inner conductor 126. More specifically, antenna body 118A is looped around an outer perimeter of the exposed portion of inner conductor 126 a plurality of times to form a spiral-shaped antenna. The tightly-coiled configuration of antenna body 118A facilitates cooling of inner conductor 126 during operation of antenna system 100A and reduces an overall size or diameter of the antenna system 100A allowing for access to smaller lumens or anatomy.

In some embodiments, antenna body 118A may have a helical shaped or helically wound coil. In some embodiments, antenna body 118A may include two tubes wound together to create a helically wound double coil. In some other embodiments, antenna body 118A may be a double-helix antenna extending along opposing sides of inner conductor 126, wound in opposite directions, along the exposed outer surface of inner conductor 126. In some embodiments, antenna body 118A may extend only partially along the exposed surface of inner conductor 126. In some other embodiments, antenna body 118A may wrap back over itself in an overlapped coil shape. In alternative embodiments, antenna body 118A may be configured in any way that facilitates operation of antenna instrument 102A as described herein.

Antenna body 118A and elongate energy transmission member 122 are disposed within a sheath 114. In this embodiment the sheath 114 is closed, sealed, or otherwise restricts fluid from passing outside of the sheath. In alternative embodiments described below, sheath 114 may have openings, slits, or otherwise be unsealed along any portion of sheath 114 to allow fluid to pass outside of the sheath.

Fluid cooling system 120 supplies cooling fluid to control the temperature along antenna instrument 102A, minimize the risk of overheating patient tissue at the target site, and/or reduce distortion of a heating zone during the ablation process. For example, the fluid cooling system may be used to prevent charring of target tissue due to an over-temperature situation of the target tissue at the target site. An over-temperature situation may result from conductive and/or radiative heating of elements of antenna system 100A and/or the target tissue during operation of antenna instrument 102A. The cooling fluid may be a liquid or a gaseous material. Fluid cooling system 120 may include a pump, a reservoir, a supply conduit 134 coupled between fluid cooling system 120 and antenna body 118A, and a return conduit 136 coupled in fluid communication between fluid cooling system 120 and body proximal end 104 of antenna instrument 102A.

In this embodiment, fluid cooling system 120 is a closed loop system. Supply conduit 134 may be coupled in fluid communication with a proximal end of antenna body 118A such that cooling fluid is supplied through antenna lumen 130 and is discharged within sheath 114 after travelling through antenna body 118A to antenna outlet 132A. The discharged fluid may then be caused to flow, for instance, from antenna outlet 132A through a return path 124 including space between antenna body 118A, elongate energy transmission member 122, and sheath 114 to return conduit 136. The fluid flow may be generated, for example, by a pressure differential between supply conduit 134 and return conduit 136.

In this example, supply conduit 134 is wrapped around outer conductor 128 in a spiral shape and extends along the outer conductor 128 to an intersection with antenna body 118A. The intersection with antenna body 118A may be near the distal end of outer conductor 128 and may be at or near the location of electrical coupling 129A. In some embodiments, the supply conduit 134 and the antenna body 118A may be formed of a continuous hollow coil having a continuous lumen. In some embodiments, the supply conduit 134 and the antenna body 118A may be connected by a coupling member. The spiral-shaped configuration of supply conduit 134 cooperates with antenna body 118A to contribute to a structural stiffness of elongate energy transmission member 122 and antenna instrument 102A. As described in later embodiments, supply conduit 134 may extend along the outer surface of outer conductor 128 substantially linearly (e.g., non-coiled) along the proximal portion 108. As described in later embodiments, fluid cooling system 120 may be an open loop system, a partially open loop system, or any other suitable type of cooling system. Fluid cooling system 120 may be a closed loop system, for example, in applications where an introduction of a foreign fluid, such as water or a saline solution, to the target site is undesirable. Examples of such types of applications may include ablation processes targeting lung tissue containing cancerous cells. Open loop and partially open loop fluid cooling systems 120 may supply a flow of cooling fluid to the target side proximal antenna outlet 132A, for example, to inhibit charring of tissue at the target site. For applications in which antenna system 100 is used as part of a microwave ablation process, hydrating the target site and/or introducing hypertonic saline solution to the target site may facilitate stabilizing a dielectric constant at the target site, facilitating consistent ablation of the target tissue. In this way, antenna body 118A and supply conduit 134 may be used in an ablation process using antenna system 100A as illustrated in FIG. 1A.

Figure 1B:
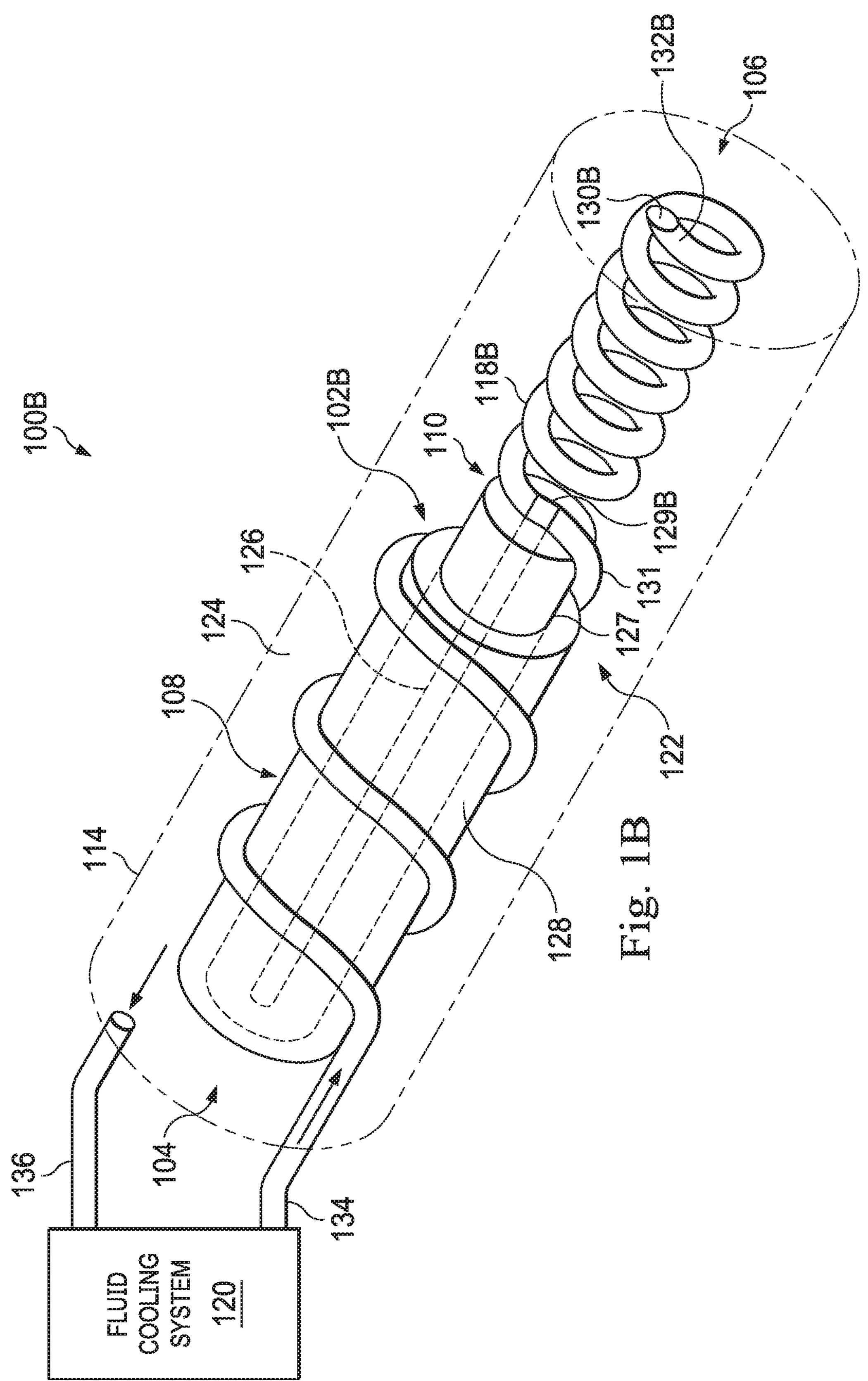
FIG. 1B illustrates an antenna system for tissue ablation with an antenna body coupled to an inner conductor according to some embodiments.

As shown in FIG. 1B, an antenna system 100B generally includes a flexible antenna instrument 102B which includes an antenna body 118B coupled to the elongate energy transmission member 122.

In this embodiment, antenna body 118B is electrically coupled (e.g., soldered) to inner conductor 126 by an electrical coupling 129B and may be used to radiate microwave energy for use in the tissue ablation process. In some embodiments, the wavelength and the frequency of the microwaves being radiated by antenna body 118B may be modified to cause a desired type of ablation at the ablation target site.

In this embodiment, antenna body 118B may be substantially similar to antenna body 118A, with differences as described. Antenna body 118B is also a conductive coiled hollow antenna that includes a lumen 130B terminating at a distal outlet 132B. The lumen 130B may have a circular cross section or any other shape providing an open lumen. In the example shown in FIG. 1B, the antenna system 100B includes the fluid cooling system 120 in fluid communication with the antenna body 118B. More specifically, the lumen 130B provides a conduit for fluid from the fluid cooling system 120 to flow to the outlet 132B. In some embodiments, antenna body 118B may have a helical shaped coil.

In this embodiment, fluid cooling system 120 is a closed loop system. Supply conduit 134 may be coupled in fluid communication with a proximal end of antenna body 118B such that cooling fluid is supplied through antenna lumen 130B and is discharged within sheath 114 after travelling through antenna body 118B to antenna outlet 132B. The discharged fluid may then be caused to flow, for instance, from antenna outlet 132B through a return path 124 including space between antenna body 118B, elongate energy transmission member 122, and sheath 114 to return conduit 136. The fluid flow may be generated, for example, by a pressure differential between supply conduit 134 and return conduit 136.

In this example, supply conduit 134 is wrapped around outer conductor 128 in a spiral shape and extends along the outer conductor 128 to an intersection with antenna body 118B. The intersection with antenna body 118B may be near the distal end of inner conductor 126 and may be at or near the location of electrical coupling 129B. All or a portion of the supply conduit 134 may be non-conductive. For example, a portion 131 distal of the outer conductor 128 and proximal of the electrical coupling 129B may be non-conductive in this embodiment. In some embodiments, the supply conduit 134 and the antenna body 118B may be formed of a continuous hollow coil having a continuous lumen. In some embodiments, the supply conduit 134 and the antenna body 118B may be connected by a coupling member. The spiral-shaped configuration of supply conduit 134 cooperates with antenna body 118B to contribute to a structural stiffness of elongate energy transmission member 122, antenna instrument 102B, and antenna system 100B. The structural stiffness of antenna system 100B may facilitate puncturing tissue as part of an ablation process. In this way, antenna body 118B and supply conduit 134 may be used in an ablation process using antenna system 100B illustrated in FIG. 1B.

Figure 1C:
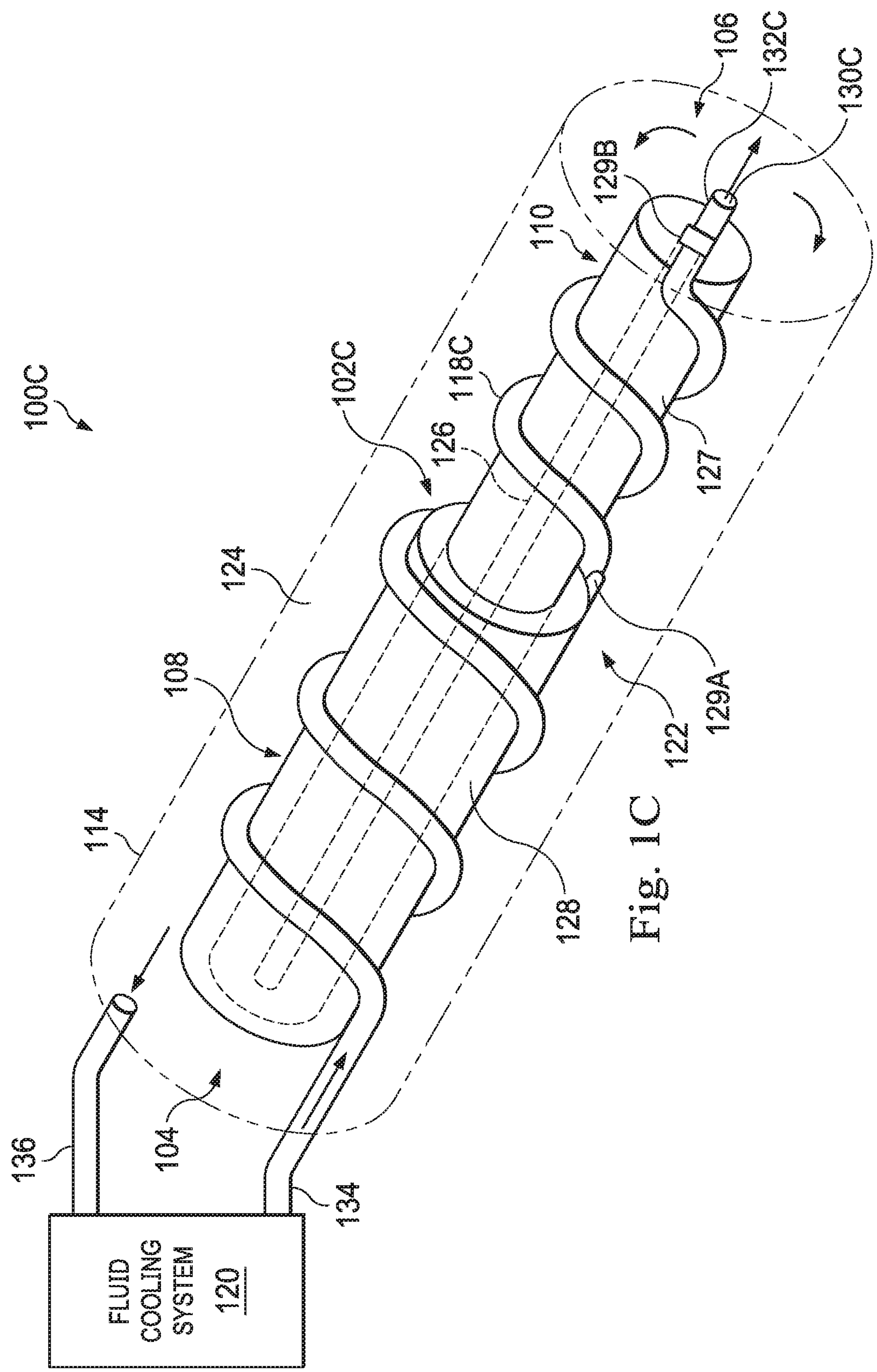
FIG. 1C illustrates an antenna system for tissue ablation with an antenna body coupled to an inner conductor and an outer conductor according to some embodiments.

As shown in FIG. 1C, an antenna system 100C generally includes a flexible antenna instrument 102C which includes an antenna body 118C coupled to the elongate energy transmission member 122.

In this embodiment, antenna body 118C is electrically coupled (e.g., soldered) to outer conductor 128 by electrical coupling 129A and to inner conductor 126 by electrical coupling 129B. Antenna body 118C may be used to radiate microwave energy for use in the tissue ablation process. In some embodiments, the wavelength and the frequency of the microwaves being radiated by antenna body 118C may be modified to cause a desired type of ablation at the ablation target site.

In this embodiment, antenna body 118C may be substantially similar to antenna bodies 118A, 118B, with differences as described. Antenna body 118C is also a conductive coiled hollow antenna that includes a lumen 130C terminating at a distal outlet 132C. The lumen 130C may have a circular cross section or any other shape providing an open lumen. In the example shown in FIG. 1C, the antenna system 100C includes the fluid cooling system 120 in fluid communication with the antenna body 118C. More specifically, the lumen 130C provides a conduit for fluid from the fluid cooling system 120 to flow to the outlet 132C. In some embodiments, antenna body 118C may have a helical shaped coil.

In this embodiment, fluid cooling system 120 is a closed loop system. Supply conduit 134 may be coupled in fluid communication with a proximal end of antenna body 118C such that cooling fluid is supplied through antenna lumen 130C and is discharged within sheath 114 after travelling through antenna body 118C to antenna outlet 132C. The discharged fluid may then be caused to flow, for instance, from antenna outlet 132C through a return path 124 including space between antenna body 118C, elongate energy transmission member 122, and sheath 114 to return conduit 136. The fluid flow may be generated, for example, by a pressure differential between supply conduit 134 and return conduit 136.

In this example, supply conduit 134 is wrapped around outer conductor 128 in a spiral shape and extends along the outer conductor 128 to an intersection with antenna body 118C. The intersection with antenna body 118C may be near the distal end of inner conductor 126 and may be at or near the location of electrical coupling 129A. In some embodiments, the supply conduit 134 and the antenna body 118C may be formed of a continuous hollow coil having a continuous lumen. In some embodiments, the supply conduit 134 and the antenna body 118C may be connected by a coupling member. The spiral-shaped configuration of supply conduit 134 cooperates with antenna body 118C to contribute to a structural stiffness of elongate energy transmission member 122, antenna instrument 102C, and antenna system 100C. The structural stiffness of antenna system 100C may facilitate puncturing tissue as part of an ablation process. In this way, antenna body 118C and supply conduit 134 may be used in an ablation process using antenna system 100C illustrated in FIG. 1C.

Figure 2A:
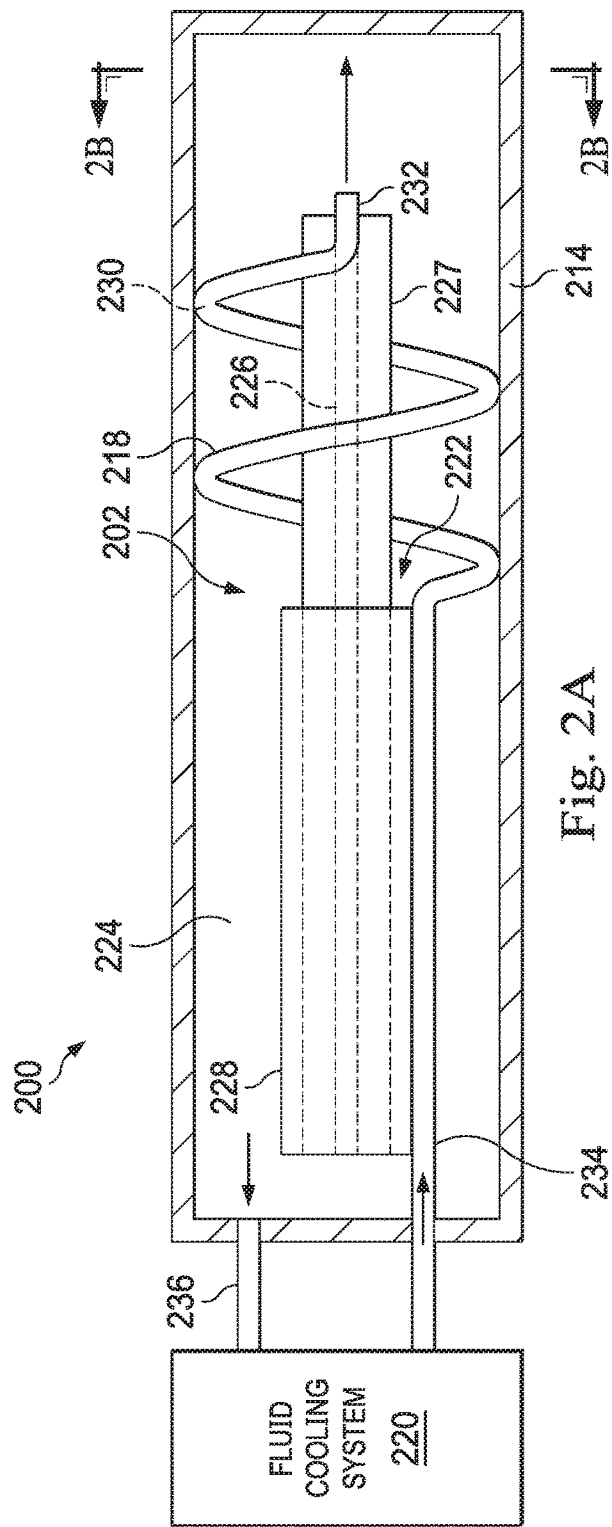
FIG. 2A is a partial cross-sectional side view of an antenna system including a linear supply conduit and a loosely-coiled hollow antenna according to some embodiments.
Figure 2B:
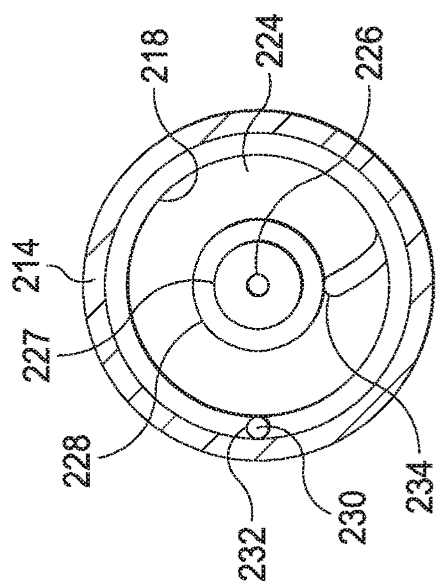
FIG. 2B is a partial cross-sectional front view of an antenna system including a linear supply conduit and a loosely-coiled hollow antenna according to some embodiments.

FIG. 2A is a cross-sectional side view of an antenna system 200 including a flexible antenna instrument 202 including a supply conduit 234 and an antenna body 218 according to some embodiments. FIG. 2B is a cross-sectional front view at a distal portion of antenna system 200. More specifically, in this embodiment, supply conduit 234 is a flexible linear supply conduit, and antenna body 218 is a loosely-coiled hollow antenna. A fluid cooling system 220 may be substantially similar to fluid cooling system 120. An elongate energy transmission member 222 including an inner conductor 226, a dielectric layer 227, and an outer conductor 228 may be substantially similar to elongate energy transmission member 122 including inner conductor 126, dielectric layer 127, and outer conductor 128. A sheath 214 may be substantially similar to sheath 114.

Antenna body 218 includes a conductive coiled hollow antenna having an antenna lumen 230 and may be substantially similar to any of the antenna bodies 118A, 118B, 118C, with the differences as described. Antenna body 218 may be electrically coupled to the inner and/or outer conductors as previously described. Antenna body 218 is coupled to, and extends distally from, supply conduit 234. Antenna body 218 is coupled to linearly-extending supply conduit 234 near a distal end of outer conductor 228 and is coiled along and spaced apart from inner conductor 226. More specifically, antenna body 218 is coil-shaped such that an outer diameter of the coil formed by antenna body 218 is substantially the same as an inner diameter of sheath 214. The cooling fluid from fluid cooling system 220 is provided to antenna lumen 230 through supply conduit 234 and travels through antenna lumen 230 to an antenna outlet 232 within sheath 214. The fluid returns through a return path 224 to a return conduit 236. In this way, antenna body 218 is cooled via both of a flow of cooling fluid internal to the antenna body 218 through the antenna lumen 230 and a flow of cooling fluid external to the antenna body 218 through the return path 224. Antenna body 218 and supply conduit 234 may be made from a single continuous piece of tubing including the lumen 230 extending therein. In this way, fabrication of antenna body 218 and supply conduit 234 is less complex, obstruction of fluid flow is minimized, and a joint between antenna body 218 and supply conduit 234 is not required. Additionally, fabricating antenna body 218 and supply conduit 234 from a single piece of continuous material may be advantageous to applications of antenna system 200 where antenna instrument 202 is exposed to corrosive or high-temperature environments, or where a substantially similar coefficient of thermal expansion within elements of antenna instrument 202 is beneficial to operation of antenna system 200. In this way, antenna body 218 and supply conduit 234 may be used in an ablation process using antenna system 200 illustrated in FIGS. 2A-2B.

Figure 3:
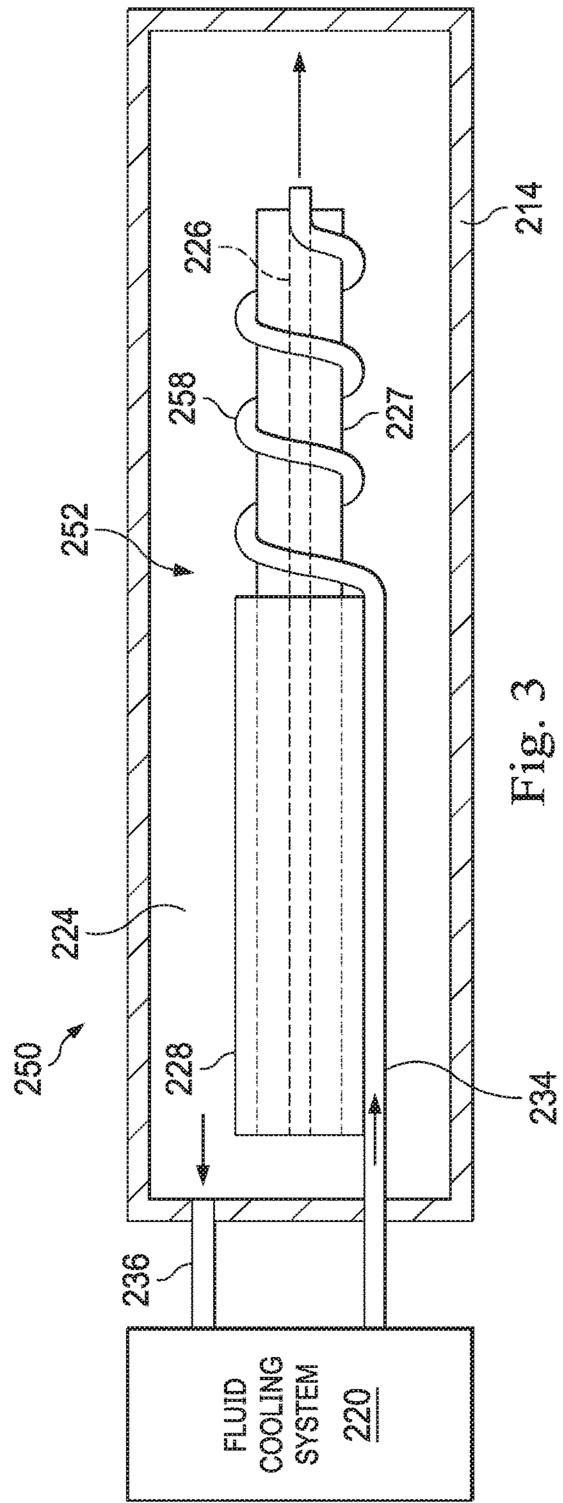
FIG. 3 is a partial cross-sectional side view of an antenna system including a linear supply conduit and a tightly-coiled hollow antenna according to some embodiments.

FIG. 3 is a cross-sectional side view of antenna system 250. Components of antenna system 250 that are substantially similar to antenna system 200 are labelled with the same numerals. In this embodiment, supply conduit 234 is a linear supply conduit, and an antenna body 258 of a flexible antenna instrument 252 is a conductive tightly-coiled hollow antenna. Antenna body 258 and supply conduit 234 may be made from a single continuous piece of tubing.

In this embodiment, antenna body 258 extends from supply conduit 234 near the distal end of outer conductor 228 and extends along an outer surface of inner conductor 226. More specifically, antenna instrument 252 is shaped such that an inner diameter of a coil formed by antenna body 258 is substantially the same as an outer diameter of inner conductor 226, and antenna body 258 contacts at least a portion of the outer surface of inner conductor 226. In this way, cooling fluid traveling through antenna body 258 cools the antenna body. Antenna body 258 contributes to cooling of inner conductor 226 through conduction as a result of the tightly-coiled arrangement of antenna body 258. In this way, antenna body 258 and supply conduit 234 may be used in an ablation process using antenna system 250 illustrated in FIG. 3.

Figure 4:
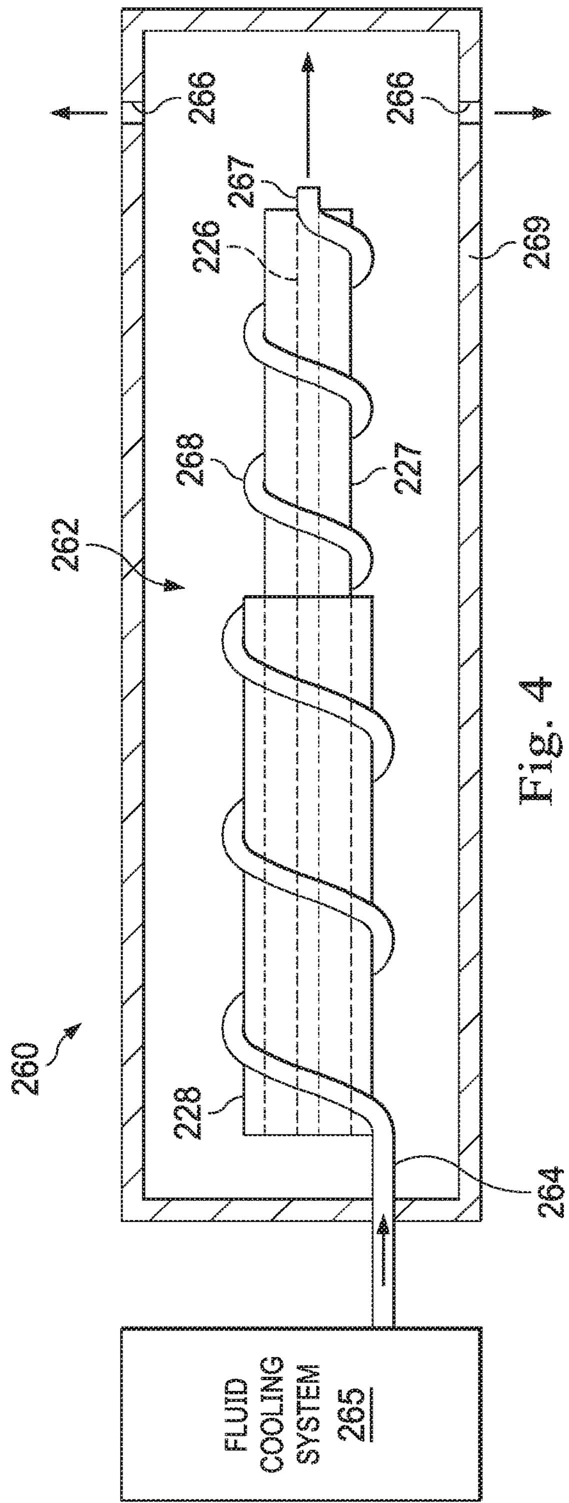
FIG. 4 is a partial cross-sectional side view of an antenna system including a tightly-coiled supply conduit, a tightly-coiled hollow antenna and an open-loop fluid cooling system according to some embodiments.

FIG. 4 is a cross-sectional side view of antenna system 260. Components of antenna system 260 that are substantially similar to antenna systems 200, 250 are labelled with the same numerals. In this embodiment, a supply conduit 264 is similar to conduit 234 with the exception that the supply conduit is a tightly-coiled supply conduit. Antenna body 268 of a flexible antenna instrument 262 is a conductive tightly-coiled hollow antenna and is similar to antenna bodies 118A, 118B, 118C, 258. In this embodiment, a fluid cooling system 265 is an open-loop fluid cooling system. Fluid cooling system 265 supplies cooling fluid through supply conduit 264, antenna body 268, an outlet 267 at a distal end of antenna body 218, and finally through outlet ports 266 extending through a sheath 269. Outlet ports 266 are positioned to discharge the cooling fluid from sheath 269 into the patient anatomy or into a device, such as a catheter, in which the antenna instrument 262 may be extended. In some embodiments, the cooling fluid discharged through outlet ports 266 may be used to flush and/or cool the ablation target site. Fluid cooling system 265 may be utilized, for example, in the open-loop configuration where bathing an ablation site in the cooling fluid is beneficial to the ablation process. In this embodiment the outlet ports are near a distal end of sheath 269, but in alternative embodiments, outlet ports may be located at any position along the surface of the sheath. In this way, antenna body 268, open-loop configuration fluid cooling system 265, and supply conduit 264 may be used in an ablation process using antenna system 260 illustrated in FIG. 4.

Figure 5:
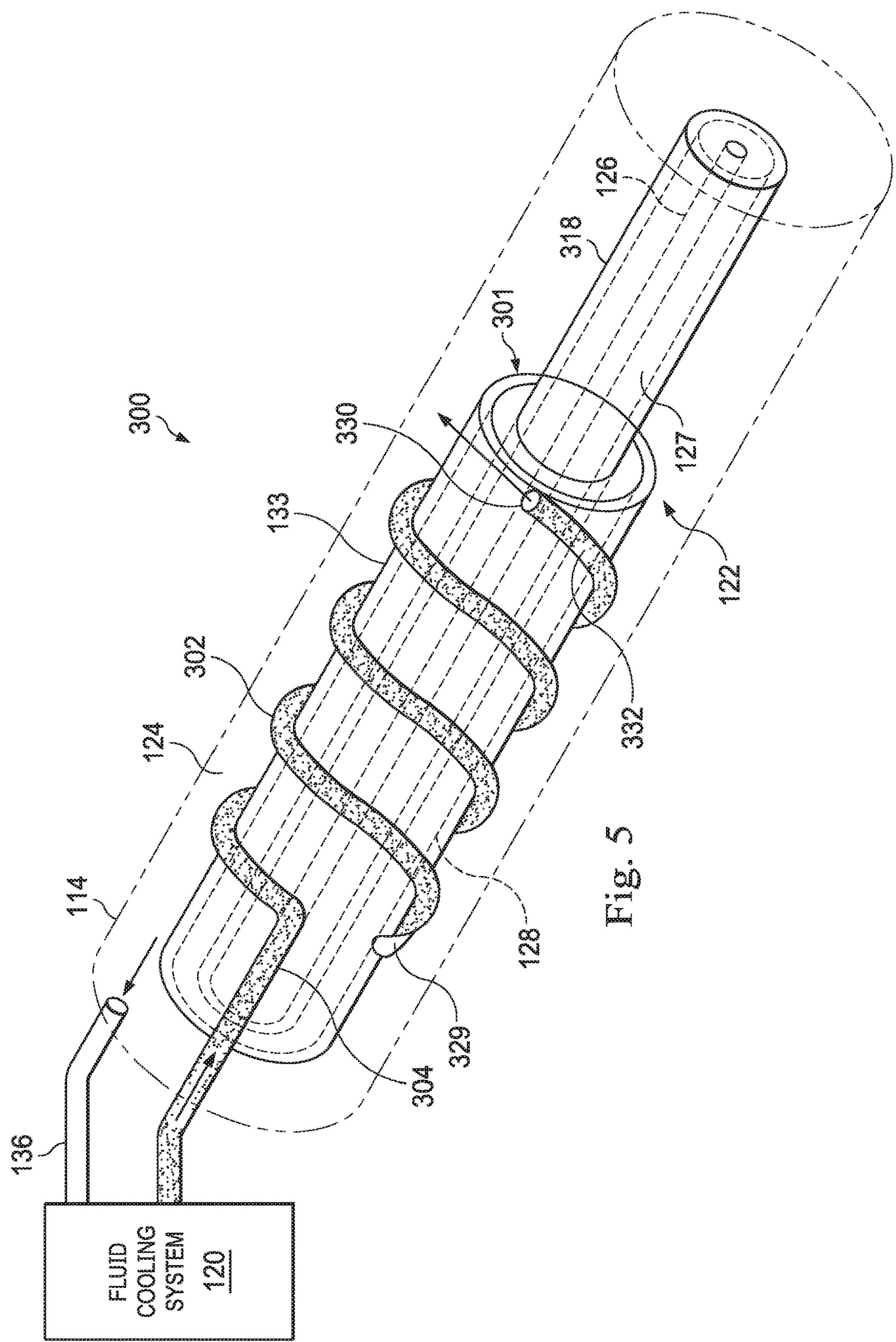
FIG. 5 illustrates an antenna system including a choke according to some additional embodiments.

FIG. 5 is a perspective view of an example of a flexible antenna instrument 301 of an antenna system 300. Components of antenna system 300 that are substantially similar to antenna systems 100A, 100B, 100C are labelled with the same numerals. Antenna system 300 includes a choke or balun 302 and an antenna body 318 according to some embodiments. An insulation layer 133 extends between the choke 302 and the outer conductor 128. In this embodiment, antenna body 318 may be formed with one or more of a variety of generally cylindrical or tubular constructions including bar and ring patterns, cutout patterns, slotted patterns, and coiled structures. In other embodiments, the antenna body may be a coiled hollow antenna body similar to antenna body 118A, 118B, 118C and supplied with cooling fluid from a dedicated supply conduit. The antenna body 318 may be electrically coupled to the outer conductor 128 or the inner conductor 126.

In this embodiment, choke 302 is a conductive hollow tightly-coiled member wrapped around a portion of the insulation layer 133 surrounding outer conductor 128. It may have a structure and cooling properties similar to those previously described above for coiled antenna bodies. In this embodiment, the choke 302 may be electrically coupled to the outer conductor 128. (e.g., soldered 329 to the outer conductor 128 through a perforation in the insulation layer 133). Choke 302 may be used to control current path and electromagnetic current path within elongate energy transmission member 122 to modify a shape of the ablation zone. The choke 302 may be insulated on non-insulated. For example, if an outer surface of the outer conductor 128 is solid or otherwise impermeable, the choke may be non-insulated and coupled directly to the outer conductor. If, for example, the outer conductor 128 has an outer surface that is braided or otherwise woven, the choke may be insulated or sealed/waterproofed.

Choke 302 is coupled in fluid communication with fluid cooling system 120 and includes a choke lumen 330 extending from fluid cooling system 120 to a choke outlet 332 such that a flow of cooling fluid may be directed through choke lumen 330 to choke outlet 332 near the distal end of outer conductor 128. Choke 302 is coupled to the fluid cooling system 120 by a supply conduit 304. The fluid discharged from choke outlet 332 may be caused to flow, for instance, from choke outlet 332 through the return path 124 between elongate energy transmission member 122 and sheath 114 to return conduit 136. The fluid flow may be generated, for example, by a pressure differential between supply conduit 304 and return conduit 136.

In some embodiments the supply conduit 304 may extend longitudinally along the elongate energy transmission member 122 from the choke to the fluid cooling system. In other embodiments, the supply conduit may be wrapped around the energy transmission member 122 from the choke to the fluid cooling system. The supply conduit 304 provides a flow of cooling fluid that cools the choke 302 and, in some embodiments, the elongate energy transmission member 122 near the supply conduit 304 and the choke 302 through a conductive process. In some embodiments, at least one of choke 302, antenna body 318, and supply conduit 134 are thermally insulated such that a conductive energy transfer does not occur between at least one of choke 302, antenna body 318, and elongate energy transmission member 122.

In some embodiments, choke 302 may be a helical-shaped coiled choke. In some other embodiments, choke 302 may be a double-helix-shaped choke extending along opposing sides of the outer surface of outer conductor 128. In some embodiments, choke 302 may include two tubes wound together to create a helically wound double coil. In some embodiments, choke 302 may extend only partially along the outer conductor 128. In some other embodiments, choke 302 may wrap back over itself in an overlapped coil shape. In this way, antenna instrument 301, choke 302, and supply conduit 304 may be used in an ablation process using antenna system 300 illustrated in FIG. 5.

Figure 6:
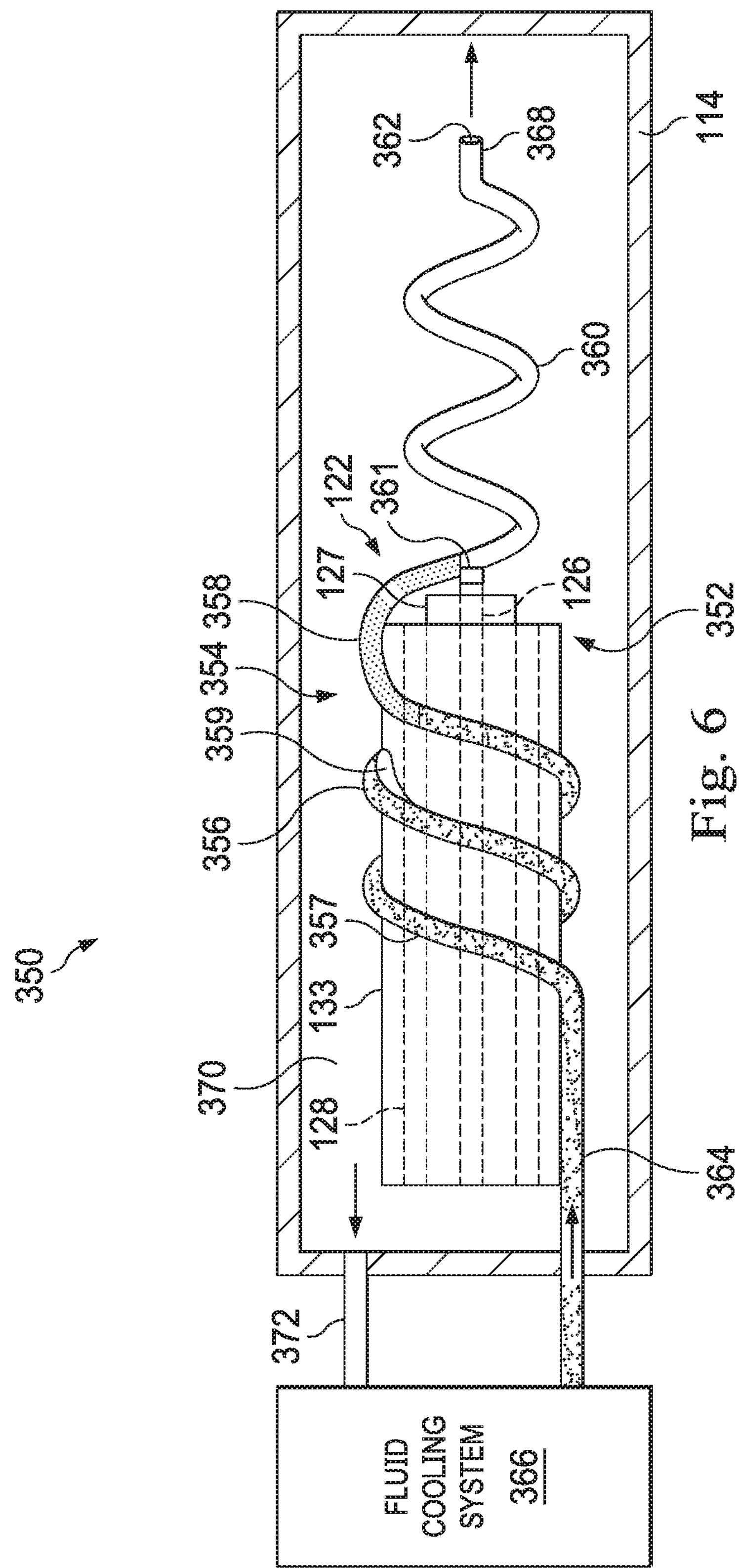
FIG. 6 is a partial cross-sectional side view of an antenna system including a tightly-coiled hybrid choke antenna according to some embodiments.

FIG. 6 is a cross-sectional side view of an antenna system 350 including a hybrid choke antenna instrument 352 according to some embodiments. Hybrid choke antenna instrument 352 includes elongate energy transmission member 122 and a coiled member 354 that includes a non-conductive portion 357, a choke portion 356, a non-conductive portion 358, and an antenna body portion 360. An insulation layer 133 may extend between the antenna body portion 360 and the outer conductor 128. The choke portion 356 is electrically coupled to the outer conductor 128 by an electrical coupling 359 (e.g., soldered to the outer conductor 128 through a perforation in the insulation layer 133). The antenna body portion 360 is electrically coupled (e.g., soldered) to inner conductor 126 by an electrical coupling 361. An A hybrid lumen 362 extends through non-conductive portion 357, choke portion 356, non-conductive portion 358, and antenna body portion 360 from a supply conduit 364 of a fluid cooling system 366 to an antenna outlet 368. After cooling fluid is passed through the coiled member 354, the discharged fluid may then be caused to flow, for instance, from antenna outlet 368 through a return path 370 including space between elongate energy transmission member 122 and sheath 114 to return conduit 372. The fluid flow may be generated, for example, by a pressure differential between supply conduit 364 and return conduit 372.

In some embodiments, portions 356, 357, 358, 360 are fabricated from an integrally formed single piece of tubular material to form coiled member 354. In some other embodiments, each of the portions 356, 357, 358, 360 are separate components that are coupled to form coiled member 354. In some embodiments, choke portion 356 and antenna body portion 360 are fabricated from the same type of conductive material, and non-conductive portion 358 and non-conductive portion 357 are fabricated from a different type of non-conductive or substantially non-conductive material. The non-conductive portions 357, 358 may include an insulator material, such as PEEK, Ultem, nylon or other plastic extrusion materials, preferable higher temperature.

Choke portion 356 is configured to operate substantially similar to choke 302. Antenna body portion 360 is configured to operate substantially similar to previously described antenna bodies. Non-conductive portion 358 is positioned between choke portion 356 and antenna body portion 360 such that antenna body portion 360 is electrically and thermally isolated from choke portion 356. In this way, non-conductive portion 358 inhibits interference between electromagnetic waves and/or energy being carried and/or emitted by choke portion 356 and antenna body portion 360. In this way, hybrid choke antenna 352 may be used in an ablation process using antenna system 200 illustrated in FIG. 6.

Figure 7:
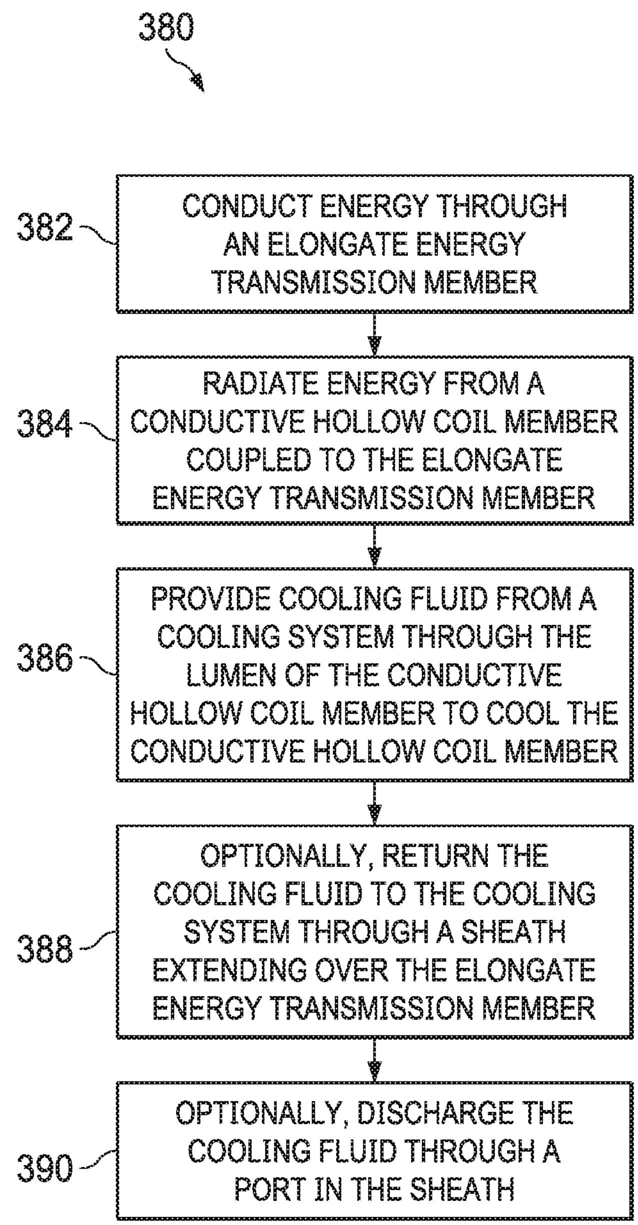
FIG. 7 illustrates a method for transferring energy to an ablation site according to some embodiments.

FIG. 7 illustrates a method 380 for transferring energy to an ablation target site according to some embodiments. The method 380 is illustrated as a set of operations or processes 382 through 388. Not all of the illustrated processes 382 through 388 may be performed in all embodiments of method 380. Additionally, one or more processes that are not expressly illustrated in FIG. 7 may be included before, after, in between, or as part of the processes 382 through 388. In some embodiments, one or more of the processes 382 through 388 may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes 382 through 388 may be performed by a control system (e.g., control system 412).

At process 382, energy is conducted through an elongate energy transmission member (e.g., elongate energy transmission member 122) of the minimally invasive ablation instrument. In some embodiments, the elongate energy transmission member is a coaxial cable and includes an inner conductor (e.g., inner conductor 126) and an outer conductor (e.g., outer conductor 128). In some embodiments in which the elongate energy transmission member includes the inner conductor and the outer conductor, a portion of the inner conductor extends from the outer conductor and through a passage bounded by a conductive hollow member (e.g., antenna body 118A, 118B, 118C) In some embodiments, the conductive hollow member is coiled around the portion of the inner conductor that extends from the outer conductor. In some embodiments, the elongate energy transmission member may be a component of an antenna instrument, as described above, that also includes an antenna body and optionally, a choke. The antenna instrument maybe extended through a catheter having a distal end positioned near an ablation target site.

At process 384, energy is radiated from a conductive hollow coil member that includes a member lumen (e.g., antenna lumen 130 and/or choke lumen 330) extending through the conductive hollow coil member. The conductive hollow coil member forms at least one loop around an outer perimeter of the elongate energy transmission member. In some embodiments, the energy is radiated from the conductive hollow coil member in the form of an electromagnetic wave of a predetermined wavelength and frequency sufficient to cause the desired ablation at the ablation target site. In some additional embodiments, an antenna body (e.g., antenna body 118A, 118B, 118C) may include the conductive hollow coil member. In some embodiments, a choke (e.g., choke 302) may include the conductive hollow coil member. In further embodiments, a hybrid choke antenna (e.g., hybrid choke antenna 352) including an antenna body portion (e.g., antenna body portion 360), a choke portion (e.g., choke 356), and an insulator portion (e.g., insulator 358) may include the conductive hollow coil member.

At process 386, a flow of cooling fluid is provided from a fluid cooling system (e.g., fluid cooling system 120) through the member lumen for cooling at least one of the conductive hollow member and the elongate energy transmission member. In some embodiments, process 386 may include providing the flow of cooling fluid through the antenna. In some other embodiments, the flow of cooling fluid is provided through the choke. In additional embodiments, the flow of cooling fluid is provided through the hybrid choke antenna.

At an optional process 388, the cooling fluid is discharged from the conductive hollow coil member into a sheath (e.g., sheath 114) extending over the elongate energy transmission member and returned to the fluid cooling system by a return apparatus (e.g., return conduit 136) coupled between the sheath and the fluid cooling system. At an optional process 390, the sheath may include at least one open port (e.g., outlet ports 266) and cooling fluid may be conveyed from the sheath through the at least one open port. In further embodiments, at least one of the radiated electromagnetic wave, the antenna body, the choke, the insulator, and the flow of cooling fluid may be modified to cause the desired ablation at the ablation target site. In some embodiments, the desired ablation at the ablation target site may include an ablation pattern including a spherical shape, an oblong shape, a rectangular shape, a linear shape, and any other type of ablation pattern that facilitates transferring energy to an ablation target site as described herein.

Figure 8:
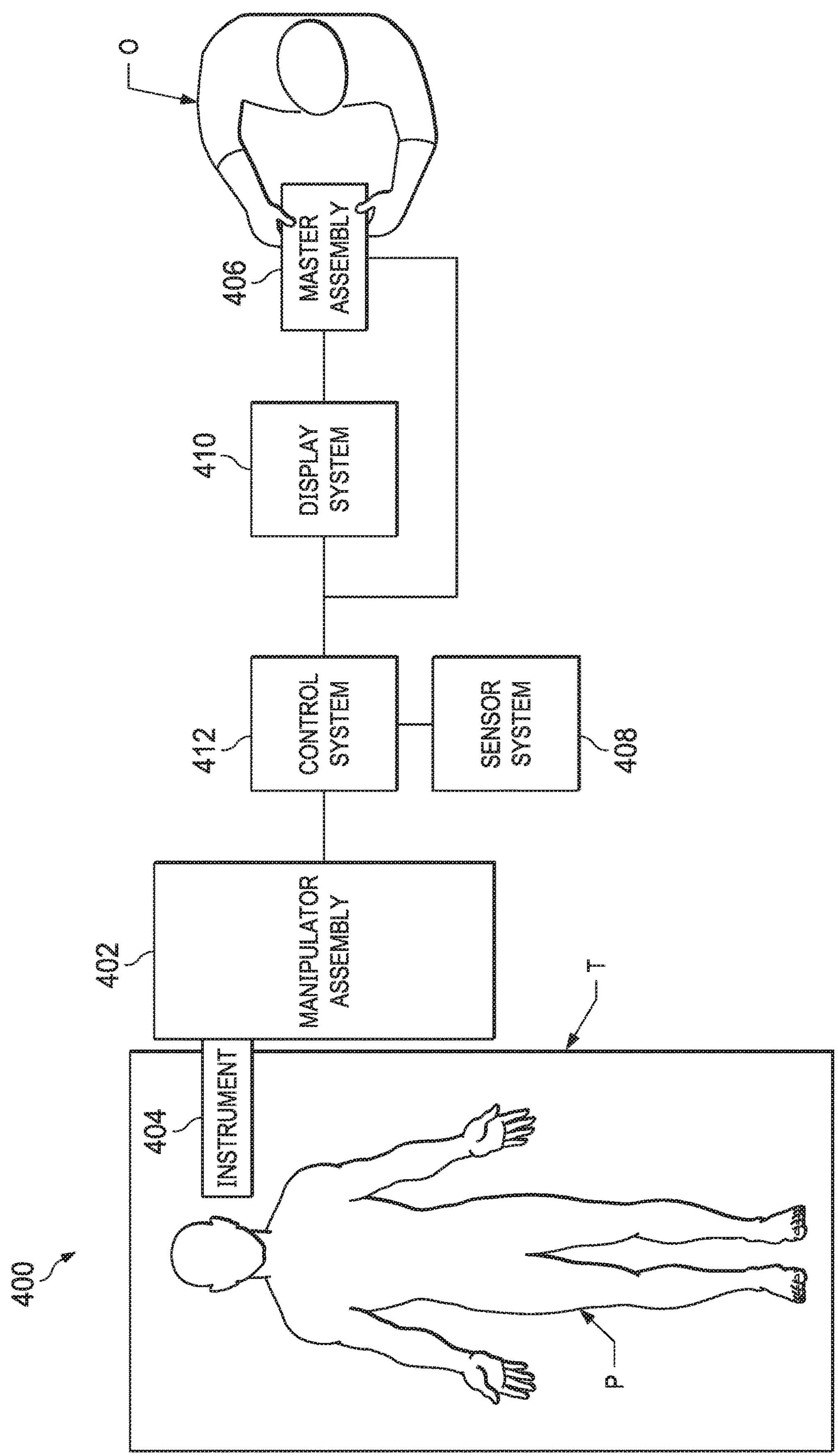
FIG. 8 is a simplified diagram of a teleoperated medical system according to some embodiments.

In various embodiments, any of the described antenna systems may be may be used as a medical instrument delivered by, coupled to, and/or controlled by a teleoperated medical system. FIG. 8 is a simplified diagram of a teleoperated medical system 400 according to some embodiments. In some embodiments, teleoperated medical system 400 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 8, medical system 400 generally includes a manipulator assembly 402 for operating a medical instrument 404 in performing various procedures on a patient P positioned on a table T. In some embodiments, the medical instrument 404 may include, deliver, couple to, and/or control any of the antenna instruments described herein. The manipulator assembly 402 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Master assembly 406 generally includes one or more control devices for controlling manipulator assembly 402. Manipulator assembly 402 supports medical instrument 404 and may optionally include a plurality of actuators or motors that drive inputs on medical instrument 404 in response to commands from a control system 412. The actuators may optionally include drive systems that when coupled to medical instrument 404 may advance medical instrument 404 into a naturally or surgically created anatomic orifice. Other drive systems may move the distal end of medical instrument 04 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 404 for grasping tissue in the jaws of a biopsy device and/or the like. Actuator position sensors such as resolvers, encoders, potentiometers, and other mechanisms may provide sensor data to medical system 400 describing the rotation and orientation of the motor shafts. This position sensor data may be used to determine motion of the objects manipulated by the actuators.

Teleoperated medical system 700 also includes a display system 710 for displaying an image or representation of the surgical site and medical instrument 704 generated by subsystems of sensor system 708 and/or any auxiliary information related to a procedure including information related to ablation (e.g. temperature, impedance, energy delivery power levels, frequency, current, energy delivery duration, indicators of tissue ablation, etc.). Display system 710 and master assembly 706 may be oriented so operator O can control medical instrument 704 and master assembly 706 with the perception of telepresence.

In some embodiments, medical instrument 404 may include components of an imaging system, which may include an imaging scope assembly or imaging instrument that records a concurrent or real-time image of a surgical site and provides the image to the operator or operator O through one or more displays of medical system 400, such as one or more displays of display system 410. The concurrent image may be, for example, a two or three-dimensional image captured by an imaging instrument positioned within the surgical site. In some embodiments, the imaging system includes endoscopic imaging instrument components that may be integrally or removably coupled to medical instrument 404. However, in some embodiments, a separate endoscope, attached to a separate manipulator assembly may be used with medical instrument 404 to image the surgical site. In some embodiments, the imaging system includes a channel (not shown) that may provide for a delivery of instruments, devices, catheters, and/or the antenna instruments described herein. The imaging system may be implemented as hardware, firmware, software or a combination thereof which interact with or are otherwise executed by one or more computer processors, which may include the processors of the control system 412.

Teleoperated medical system 400 may also include control system 412. Control system 412 includes at least one memory and at least one computer processor (not shown) for effecting control between medical instrument 404, master assembly 406, sensor system 408, and display system 410. Control system 412 also includes programmed instructions (e.g., a non-transitory machine-readable medium storing the instructions) to implement some or all of the methods described in accordance with aspects disclosed herein, including instructions for providing information to display system 410.

Control system 412 may optionally further include a virtual visualization system to provide navigation assistance to operator O when controlling medical instrument 404 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

Figures 9A, 9B:
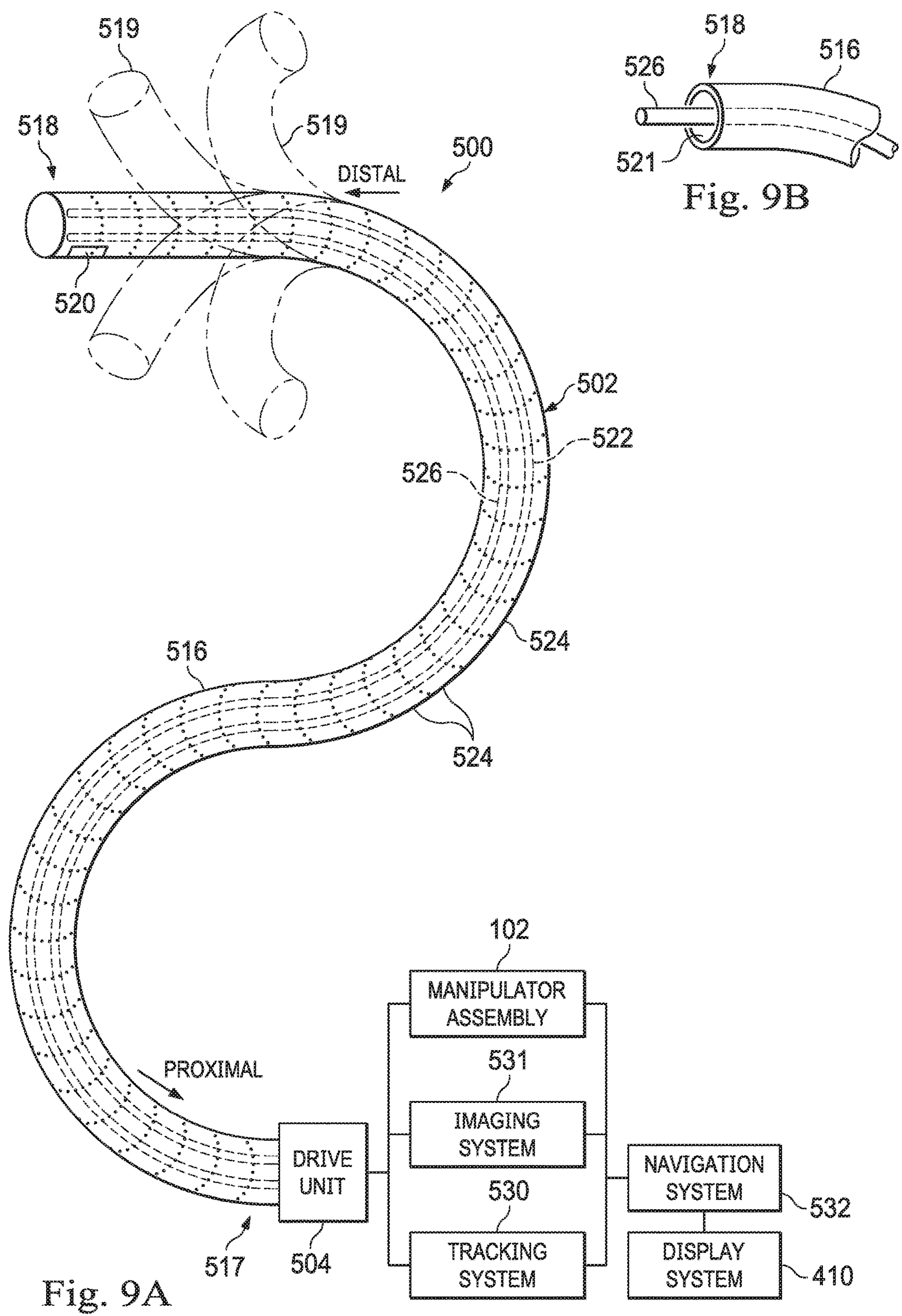
FIG. 9A is a simplified diagram of a medical instrument system according to some embodiments.
FIG. 9B is a simplified diagram of a medical instrument with an extended medical tool according to some embodiments.

FIG. 9A is a simplified diagram of a medical instrument system 500 according to some embodiments. Medical instrument system 500 includes elongate device 502, such as a flexible catheter, coupled to a drive unit 504. Elongate device 502 includes a flexible body 516 having proximal end 517 and distal end or tip portion 518. Medical instrument system 500 further includes a tracking system 530 for determining the position, orientation, speed, velocity, pose, and/or shape of distal end 518 and/or of one or more segments 524 along flexible body 516 using one or more sensors and/or imaging devices as described in further detail below.

Tracking system 530 may optionally track distal end 518 and/or one or more of the segments 524 using a shape sensor 522. Shape sensor 522 may optionally include an optical fiber aligned with flexible body 516 (e.g., provided within an interior channel (not shown) or mounted externally). The optical fiber of shape sensor 522 forms a fiber optic bend sensor for determining the shape of flexible body 516. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. In some embodiments, tracking system 530 may optionally and/or additionally track distal end 518 using a position sensor system 520. Position sensor system 520 may be a component of an EM sensor system with position sensor system 520 including one or more conductive coils that may be subjected to an externally generated electromagnetic field. In some embodiments, position sensor system 520 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, an optical fiber sensor may be used to measure temperature or force. In some embodiments, a temperature sensor, a force sensor, an impedance sensor, or other types of sensors may be included within the flexible body.

Flexible body 516 includes a channel 521 sized and shaped to receive a medical instrument 526. In various embodiments, any of the antenna instruments and sheaths described above may be inserted through the channel 521 of the flexible body 516. FIG. 9B is a simplified diagram of flexible body 516 with medical instrument 526 extended according to some embodiments. In some embodiments, medical instrument 526 may be used for procedures such as imaging, visualization, surgery, biopsy, ablation, illumination, irrigation, or suction. Medical instrument 526 can be deployed through channel 521 of flexible body 516 and used at a target location within the anatomy. Medical instrument 526 may include, for example, image capture probes, biopsy instruments, laser ablation fibers, and/or other surgical, diagnostic, or therapeutic tools. Medical instrument 526 may be used with an imaging instrument (e.g., an image capture probe) also within flexible body 516. The imaging instrument may include a cable coupled to the camera for transmitting the captured image data. In some examples, the imaging instrument may be a fiber-optic bundle, such as a fiberscope, that couples to image processing system 531. The imaging instrument may be single or multi-spectral, for example capturing image data in one or more of the visible, infrared, and/or ultraviolet spectrums. Medical instrument 526 may be advanced from the opening of channel 521 to perform the procedure and then retracted back into the channel when the procedure is complete. Medical instrument 526 may be removed from proximal end 517 of flexible body 516 or from another optional instrument port (not shown) along flexible body 516.

Flexible body 516 may also house cables, linkages, or other steering controls (not shown) that extend between drive unit 504 and distal end 518 to controllably bend distal end 518 as shown, for example, by broken dashed line depictions 519 of distal end 518. In some examples, at least four cables are used to provide independent "up-down" steering to control a pitch of distal end 518 and "left-right" steering to control a yaw of distal end 518. Steerable elongate devices are described in detail in U.S. patent application Ser. No. 13/274,208 (filed Oct. 14, 2011) (disclosing "Catheter with Removable Vision Probe"), which is incorporated by reference herein in its entirety.

The information from tracking system 530 may be sent to a navigation system 532 where it is combined with information from image processing system 531 and/or the preoperatively obtained models to provide the operator with real-time position information. In some examples, the real-time position information may be displayed on display system 410 of FIG. 8 for use in the control of medical instrument system 500. In some examples, control system 412 of FIG. 8 may utilize the position information as feedback for positioning medical instrument system 500. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 500 may be teleoperated within medical system 400 of FIG. 8. In some embodiments, manipulator assembly 402 of FIG. 8 may be replaced by direct operator control. In some examples, the direct operator control may include various handles and operator interfaces for hand-held operation of the instrument.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Medical tools that may be delivered through the flexible elongate devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of antenna instrument 102. Steerable instruments are described in detail in U.S. Pat. No. 7,416,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The systems described herein may be suited for navigation and treatment of anatomic tissues, via natural or surgically created connected passageways, in any of a variety of anatomic systems, including the lung, colon, stomach, the intestines, the kidneys and kidney calices, bladder, liver, gall bladder, pancreas, spleen, the ureter, ovaries, uterus, the brain, the circulatory system including the heart, vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An antenna system for tissue ablation, the antenna system comprising:
- an energy transmission member comprising an inner conductor, an outer conductor, and a dielectric layer between the inner and outer conductors, wherein a portion of the dielectric layer extends distally of a distal end of the outer conductor;
- a conductive hollow coil member including a member lumen within a length of the conductive hollow coil member, wherein the conductive hollow coil member is coiled around the portion of the dielectric layer and is separate from the inner conductor of the energy transmission member, wherein the conductive hollow coil member extends along an entire length of the outer conductor of the energy transmission member; and
- a fluid cooling system coupled to the conductive hollow coil member for providing a flow of a cooling fluid through the member lumen for cooling the conductive hollow coil member.

2. The antenna system of claim 1, wherein the conductive hollow coil member includes at least one of an antenna body or a choke member.

3. The antenna system of claim 1, further comprising a sheath extending over the energy transmission member and the conductive hollow coil member.

4. The antenna system of claim 3, wherein the sheath provides a return path for the cooling fluid.

5. The antenna system of claim 3, wherein the sheath includes an open distal outlet port through which the cooling fluid is conveyed.

6. The antenna system of claim 1, wherein the conductive hollow coil member is coupled to the outer conductor.

7. The antenna system of claim 6, wherein the conductive hollow coil member is coupled to the inner conductor.

8. The antenna system of claim 6, wherein the inner conductor extends at least partially through a passage bounded by the conductive hollow coil member.

9. The antenna system of claim 1, further comprising a conduit configured to couple the fluid cooling system to the conductive hollow coil member.

10. The antenna system of claim 9, wherein the conduit is integrally formed with the conductive hollow coil member.

11. The antenna system of claim 1, wherein the conductive hollow coil member is wrapped around the outer conductor of the energy transmission member.

12. The antenna system of claim 1, wherein the energy transmission member is flexible.

13. An antenna system for tissue ablation, the antenna system comprising:
- an energy transmission member including an inner conductor, an outer conductor, and an insulator disposed between the inner and outer conductors;
- an antenna body coupled to the energy transmission member, the antenna body being separate from the inner conductor;
- a choke including a conductive hollow coil member coiled around and contacting the insulator, the conductive hollow coil member including a member lumen within a length of the conductive hollow coil member and adapted to convey a cooling fluid;
- a fluid cooling system for providing a flow of the cooling fluid through the member lumen for cooling the conductive hollow coil member; and
- a conduit extending along the energy transmission member configured to couple the fluid cooling system to the conductive hollow coil member, wherein the conduit is integrally formed with the conductive hollow coil member and is wound around the energy transmission member.

14. The antenna system of claim 13 wherein the choke includes an insulation material.

15. The antenna system of claim 13, wherein the choke is coupled to the outer conductor.

16. A method of transferring energy to an ablation target site, the method comprising:
- conducting energy through an energy transmission member comprising an inner conductor, an outer conductor, and a dielectric layer separating the inner and outer conductors, wherein a portion of the dielectric layer extends beyond the outer conductor at a distal end of the energy transmission member;
- radiating energy from a conductive hollow coil member, wherein the conductive hollow coil member includes a member lumen within the conductive hollow coil member, wherein the conductive hollow coil member is coiled around the portion of the dielectric layer and is separate from the inner conductor of the energy transmission member, and wherein the conductive hollow coil member extends along an entire length of the outer conductor of the energy transmission member; and
- providing a flow of a cooling fluid from a fluid cooling system through the member lumen for cooling the conductive hollow coil member.

17. The method of claim 16, wherein radiating the energy from the conductive hollow coil member comprises radiating the energy from at least a portion of an antenna body.

18. The method of claim 16, wherein conducting the energy through the energy transmission member comprises conducting the energy through at least one of the inner conductor or the outer conductor, and wherein the conductive hollow coil member is coupled to the outer conductor.

19. The method of claim 16, further comprising returning the cooling fluid to the fluid cooling system through a sheath extending over the energy transmission member and the conductive hollow coil member.

20. The method of claim 19, further comprising conveying the cooling fluid from the sheath through at least one open distal outlet port.

* * * * *